(12) United States Patent
Moore (10) Patent No.: US 9,440,059 B2
(45) Date of Patent: Sep. 13, 2016

(54) ADJUSTABLE DIAMETER HEMOSTATIC VALVE

(75) Inventor: William F. Moore, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 475 days.

(21) Appl. No.: 13/409,496

(22) Filed: Mar. 1, 2012

(65) Prior Publication Data

US 2012/0238958 A1 Sep. 20, 2012

Related U.S. Application Data

(60) Provisional application No. 61/454,087, filed on Mar. 18, 2011.

(51) Int. Cl.
*A61M 5/178* (2006.01)
*A61M 5/00* (2006.01)
*A61M 39/06* (2006.01)

(52) U.S. Cl.
CPC ................ *A61M 39/0613* (2013.01)

(58) Field of Classification Search
CPC ............ A61M 2039/0673; A61M 2039/0633; A61M 39/228; A61M 2039/062; A61M 39/06; A61M 2039/0626; A61M 39/0613; A61B 2017/00477; A61B 17/3462; F16K 7/02; F16K 7/08; F16K 3/03; F16K 7/07
USPC .................................................. 604/167.03
See application file for complete search history.

(56) References Cited

U.S. PATENT DOCUMENTS

| | | | |
|---|---|---|---|
| 2,321,336 A | 6/1943 | Tondreau | 251/18 |
| 3,329,390 A | 7/1967 | Hulsey | 251/4 |
| 4,580,573 A | 4/1986 | Quinn | 128/657 |
| 5,059,186 A | 10/1991 | Yamamoto et al. | 604/280 |

(Continued)

FOREIGN PATENT DOCUMENTS

| | | |
|---|---|---|
| FR | 2 439 022 A1 | 5/1980 |
| FR | 2 863 504 A1 | 6/2005 |

(Continued)

OTHER PUBLICATIONS

W.L Gore & Associates, Inc. brochure, "Better Control, Minimized Blood Loss. Featuring the Gore@ DrySeal Valve, Performance by design, Gore DrySeal Sheath," Apr. 2010, 4 pgs., AP0201-EN1; © W.L.Gore & Associates, Inc. Flagstaff, AZ.

(Continued)

*Primary Examiner* — Jason Flick
(74) *Attorney, Agent, or Firm* — Brinks Gilson & Lione (57) ABSTRACT

A hemostatic valve device for use in inserting an interventional device into a body lumen of a patient. The valve device includes a housing that defines a cavity between first and second end openings. A valve structure is disposed within the cavity, and defines a variable diameter channel for receiving the interventional device. An annular chamber is generally formed between the valve structure and the housing inner surface, and can be filled with fluid. The housing is movable between first and second positions so that the volume of the cavity and the diameter of the channel vary to a degree for the valve structure to form a seal along the interventional device inserted within the channel. The valve structure may be configured to seal without substantial twisting.

15 Claims, 7 Drawing Sheets

(56) References Cited

U.S. PATENT DOCUMENTS

| | | | |
|---|---|---|---|
| 5,071,411 A * | 12/1991 | Hillstead | 604/246 |
| 5,158,553 A | 10/1992 | Berry et al. | 604/248 |
| 5,161,773 A | 11/1992 | Tower | 251/5 |
| 5,211,370 A | 5/1993 | Powers | 251/4 |
| 5,338,313 A * | 8/1994 | Mollenauer et al. | 604/249 |
| 5,360,417 A | 11/1994 | Gravener et al. | 604/278 |
| 6,152,933 A | 11/2000 | Werp et al. | |
| 6,276,661 B1 * | 8/2001 | Laird | A61B 17/3462 137/317 |
| 6,602,240 B2 * | 8/2003 | Hermann | A61B 17/3462 251/4 |
| 6,860,463 B2 | 3/2005 | Hartley | 251/4 |
| 7,118,086 B1 | 10/2006 | Borglum et al. | |
| 7,172,580 B2 | 2/2007 | Hruska et al. | 604/248 |
| 7,435,253 B1 | 10/2008 | Hartley et al. | 623/1.12 |
| 2005/0171479 A1 | 8/2005 | Hruska et al. | 604/167.06 |
| 2007/0078395 A1 | 4/2007 | Valaie | 604/164.01 |
| 2008/0157017 A1 | 7/2008 | Macatangay et al. | 251/314 |
| 2009/0024137 A1 | 1/2009 | Chuter et al. | 606/108 |
| 2009/0118681 A1 | 5/2009 | Molgaard-Nielsen | |

FOREIGN PATENT DOCUMENTS

| | | |
|---|---|---|
| JP | 2001-506156 A | 5/2001 |
| JP | 2011-502001 A | 1/2011 |
| WO | WO 00/24453 A2 | 5/2000 |
| WO | WO 2004/045386 A2 | 6/2004 |
| WO | WO 2005/058409 A1 | 6/2005 |
| WO | WO 2010/028021 A1 | 3/2010 |
| WO | WO 2011/143066 A1 | 11/2011 |

OTHER PUBLICATIONS

Extended European Search Report for related application No. EP 12159752.0, dated Apr. 10, 2015, 7 pgs.

Office Action and English translation for corresponding JP Application No. 2012-058099 dated Aug. 18, 2015, 8 pages.

* cited by examiner

ADJUSTABLE DIAMETER HEMOSTATIC VALVE

RELATED APPLICATION

The present patent document claims the benefit of the filing date under 35 U.S.C. §119(e) of Provisional U.S. Patent Application Ser. No. 61/454,087, filed Mar. 18, 2011, which is hereby incorporated by reference.

BACKGROUND

The present disclosure relates to medical devices and procedures. In particular, it relates to hemostatic valves and systems, and methods of using the same.

Numerous procedures have been developed that involve the percutaneous insertion of a medical device into a body vessel of a patient's body. Such a device may be introduced into the vessel by a variety of known techniques. For example, a wire guide may be introduced into a vessel using the Seldinger technique. This technique involves creating a surgical opening in a vessel with a needle and inserting a wire guide into the vessel through a bore of the needle. The needle can be withdrawn, leaving the wire guide in place. An introducer device is then inserted over the wire guide and into the vessel. The introducer device may be used in conventional fashion to insert into the body vessel a variety of medical devices, such as catheters, cardiac leads, balloons, stents, stent grafts, and the like.

For example, an introducer device may be used to deliver and deploy an endoluminal prosthesis, such as a stent or stent graft, to treat a damaged or diseased body lumen such as a bile duct or a blood vessel. The deployment of the endoluminal prosthesis into the lumen of a patient from a remote location by the use of an introducer delivery and deployment device is well known in the art. For example, U.S. Pat. No. 7,435,253 entitled "A Prosthesis and a Method and Means of Deploying a Prosthesis," which is incorporated herein by reference in its entirety, proposes a delivery and deployment system for an endoluminal prosthesis. The prosthesis is radially compressed onto a delivery catheter and is covered by an outer sheath. To deploy the system, the operator slides the outer sheath over the delivery catheter, thereby exposing the prosthesis for outward expansion thereof.

One of the challenges associated with endoluminal procedures is controlling the flow of bodily fluids within the introducer device during the procedure. Valve devices may be provided when it is necessary or desired to control fluid flow. For example, the introducer device may include a hemostatic valve to limit or prevent blood loss through the introducer device during a procedure. Various hemostatic valve devices have been described in the patent literature. U.S. Pat. App. Publ. No. 2007/0078395 A1, which is incorporated herein by reference in its entirety, for example, discloses numerous examples of hemostatic valve devices and systems that use disk valves to control fluid flow.

Another type of hemostatic valve device that is presently in use for sealing elongated passages in a medical device to prevent loss of blood is known as an iris valve. An iris valve is described in U.S. Pat. No. 5,158,553, which is incorporated herein by reference in its entirety. The valve described in the '553 patent comprises a valve hub that is joined to a catheter-type device, and a rotatable cap that is joined to the hub. An elastomeric sleeve is positioned in an opening through the interior of the valve body. Each end of the elastomeric sleeve is joined to the rotatable cap by wrapping and clamping the respective end around a clamping mechanism. When the cap is rotated in a first direction, the circular opening of the elastomeric sleeve is fully opened. When the cap is rotated in a second direction opposite the first direction, the elastomeric sleeve is twisted intermediate the two ends to effect closure of the circular opening. Due to the elastomeric properties of the sleeve, the circular opening of the elastomeric sleeve constricts as the cap is rotated to effect closure.

Although the valve of the '553 patent is generally effective for sealing sheaths of certain sizes and compositions, the general design of the valve assembly of the '553 patent has certain shortcomings. For example, the manner of engaging the ends of the seal to the respective hub and cap is less than optimal. Such ends are capable of disengagement, which destroys the ability of the valve to form a seal. In addition, the seal does not include provisions to prevent recoil of the seal after rotation of the rotatable cap to position the seal in a desired position. As a result, if the operator relaxes the rotational pressure on the valve, the seal can revert, or recoil, to its original (unsealed) position. Yet another problem with the iris valve assembly as described in the '553 patent is that longitudinally extending gaps or channels are capable of being formed along the seal, which gaps or channels can extend through the valve after rotation of the valve to the closed position. When such gaps or channels are present, fluid can leak through them in the valve seal. Furthermore, the configuration of such valves renders them subject to tearing. As shown in FIG. 5 of the '553 patent, only a small portion of the entire iris valve assembly forms the seal along the sheath, e.g., less than about 20% of the length of the elastomeric sleeve.

Often, a single introducer device may be used to insert multiple medical devices during a single procedure. For example, a single introducer sheath with a hemostatic valve device may be used first for introducing a delivery catheter for deployment of an endoluminal prosthesis within a vessel. Once the prosthesis is placed within the vessel, the single introducer sheath with the hemostatic valve device is also used to deliver an interventional catheter, such as a balloon catheter, to the vessel to cause expansion of the deployed prosthesis. In this example, the hemostatic valve device must be able to provide a hemostatic seal under at least three distinct conditions: 1) to seal against the delivery catheter carrying the endoluminal prosthesis when inserted in the introducer sheath and valve device; 2) to seal when the delivery catheter is removed from the introducer sheath and valve device; and 3) to seal against the interventional catheter when inserted in the introducer sheath and valve device.

One problem with using a single introducer device for multiple medical devices is that each medical device can have a different diameter. Thus, the ideal hemostatic valve device will be able to accommodate and seal over a wide range of diameters of the medical devices. For example, it may be advantageous for a hemostatic valve device to seal well around the surface of a delivery catheter, as well as a wire guide that is 50%, 25%, 10%, or smaller in diameter relative to the diameter of the delivery catheter, or to seal even when there is no device present. Moreover, such a hemostatic valve device should be able to adjust quickly to large variations in diameter.

SUMMARY

In one embodiment, a hemostatic valve device for use in inserting an interventional device into a body lumen of patient is provided. In one example, the hemostatic valve can include a housing and a valve structure. The housing can have a first end opening, a second end opening, and an interior surface defining a cavity between the first and second end openings. The valve structure can be disposed within the cavity and coupled to the housing to define an annular chamber within the housing cavity. An inner radial surface of the valve structure defines a longitudinal tubular channel within the cavity between the first and second end openings for receiving an interventional device. The annular chamber may include a fluid, which may be a substantially incompressible fluid. The housing is movable between a first position and a second position. In the first position, the cavity has a first volume and the channel has a first diameter, while in the second position, the first and second end openings are closer to one another, the cavity has a second lesser volume and the channel has a second lesser diameter.

In another example, a hemostatic valve device can include a housing and a bladder structure. The housing can have a first end opening, a second end opening, and an interior surface defining a cavity disposed between the first and second end openings. The housing can include an end cap and a main housing body. The bladder structure can be disposed within the cavity and extended between the end cap and the housing body. The bladder structure can have an inner radial surface defining a channel within the cavity between the first and second end openings. The bladder structure can be arranged within the cavity of the housing to define an annular chamber of a substantially constant volume. A fluid can be disposed within the annular chamber. Relative axial movement between the end cap and the cannula body can vary a volume of the housing cavity and can displace the bladder structure between an open configuration and a sealed configuration to move the channel between a first diameter and a second diameter, respectively.

In one aspect, the valve structure may include a first end coupled to the end cap and a second end coupled to the cannula body. The second end of the valve structure can be securely fixed to the cannula body, and the first end of the valve structure can be coupled to the end cap in a manner to inhibit substantial twisting of the valve structure during relative axial movement between the end cap and the cannula body. In another aspect, the first end of the valve structure can include a ring segment that is configured to remain in engagement with the interior surface of the housing during relative movement of the housing components. The interior surface of the housing may include an inner groove formed therein, and the valve member may include a sealing member disposed along a portion of the ring segment and received within the inner groove to form a mechanical seal between the valve member and the housing.

In another example, a hemostatic valve device can include a means for varying the volume of a housing cavity. A valve member can be disposed within the housing cavity and coupled to the housing to define an annular chamber within the housing cavity. The valve member can have an inner radial surface to define a channel within the housing cavity extending at least partially between the first and second end openings. The valve member may have a substantially incompressible fluid sealed within the annular chamber thereof. The volume varying means is configured to move the valve member between an open configuration and a sealed configuration to vary a diameter of the channel.

DETAILED DESCRIPTION OF PREFERRED EMBODIMENTS

Throughout the specification, when referring to a medical device, or a portion of a medical device, the terms "distal" and "distally" shall denote a position, direction, or orientation that is generally towards, or in the direction of, the patient when the device is in use. The terms "proximal" and "proximally" shall denote a position, direction, or orientation that is generally away from the patient, or closer to the operator, during use of the device.

Figure 1:
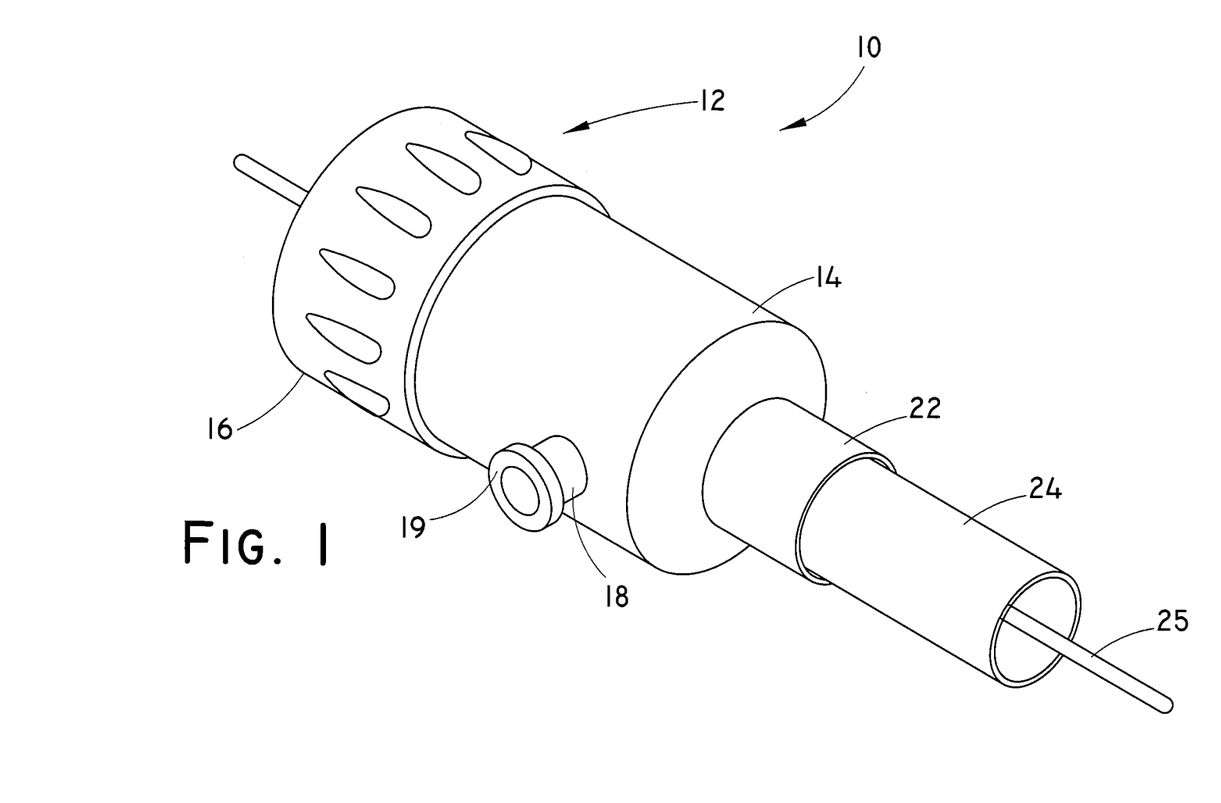
FIG. 1 is a perspective view of a hemostatic valve device.

FIG. 1 illustrates a perspective view of a hemostatic valve assembly 10. The valve assembly 10 includes a valve housing 12 having a cannula body 14 and an end cap 16. The cannula body 14 and the end cap 16 may be sealably coupled to one another. The valve housing 12 may also include a side-arm spout 18 extending in a generally transverse direction from the cannula body 14. The spout 18 may be used for supplying or removing a fluid in a conventional fashion, and preferably includes a lip 19 sized and shaped for threaded or like engagement with a tube or other device (not shown). The distal end of the cannula body 14 may have a smaller diameter portion 22 for use in attaching the valve assembly 10 to an interventional device. The interventional device 24 can extend distally from the smaller diameter portion 22 of the valve housing 12 in a conventional fashion. Further, a wire guide 25 can extend through the valve assembly 10.

The term "interventional device" refers to any device, object, or structure, that supports, repairs, or replaces, is configured to support, repair, or replace, or that may be used, alone or in combination with other devices, objects, or structures, to support, repair, or replace a body part or a function of that body part. Examples of interventional devices include, but are not limited to, sheaths, catheters, wire guides, cardiac leads, vessel occlusion devices, filters, stents, stent grafts, and delivery and deployment devices.

Figure 2:
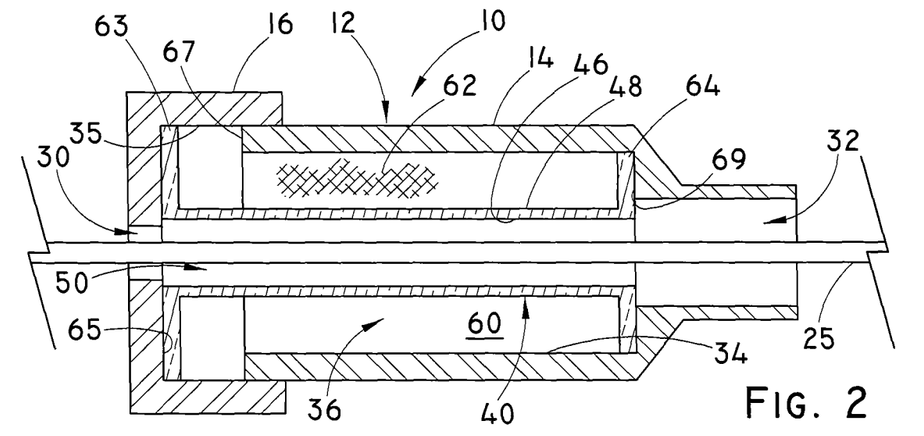
FIG. 2 is a cross-sectional view of a hemostatic valve device, with a valve structure in an open position.

FIG. 2 is an exemplary transverse cross-sectional view of the valve assembly 10 (without the interventional device 24). The valve housing 12 includes a proximal end opening 30 and a distal end opening 32. An interior surface 34 of the cannula body 14 and an interior surface 35 of the end cap 16 can define a housing cavity 36 between the proximal and distal end openings 30, 32. A valve or bladder structure 40 is disposed within the housing cavity 36. The valve structure 40 can be movable between an open position and a closed, sealed position as described below. The valve structure 40 can have an inner radial surface 46 separated from an outer radial surface 48 by a wall thickness. The inner radial surface 46 can define a longitudinal channel 50 about a channel axis within the housing cavity 36 between the proximal and distal end openings 30, 32. The channel 50 is configured for receiving one or more interventional devices, and can be formed to have a tubular cylindrical surface approximately equal to the longitudinal length of the valve housing 40 to seal along a length of the interventional device. The diameter of the channel can vary between a first diameter and a second, lesser diameter, where the valve structure may completely close in on itself to form a seal when an interventional device is not disposed in the channel.

The valve structure 40 can be one of many shapes and sizes. In one example, as shown in FIG. 2, the valve structure 40 can be a tubular member having portions such as proximal and distal end portions 63, 64 coupled to at least one of the interior surface 35 of the end cap 16 and the interior surface 34 of the cannula body 14. The outer radial surface 48 of valve structure 40 together with the interior surface 34 of the cannula body 14 and the interior surface 35 of the end cap 16 can define a valve chamber 60 having an annular shape that fills a portion of the volume of the housing cavity 36. The valve chamber 60 can be filled with a pre-determined amount of fluid 62, preferably a substantially incompressible fluid, which can be sealed within the valve structure, hence creating a fluid-tight chamber. Examples of such fluid include saline, water, gel-like substances such as saline gel or mineral oil gel, or other biocompatible fluids or gels. However, it is possible to use compressible fluids such as air or other gases. To this end, the valve assembly 10 may be a closed, self-contained system without the necessity of an external means for introducing fluid within the valve structure. Alternatively, the valve assembly 10 can be an open system, which can allow the introduction of fluids with different densities. For example, a foamed saline can be introduced through the open spout 18 that is in communication with the valve chamber 60, after which the spout is sealably closed. The foamed saline can impart some elasticity to the valve structure to facilitate creating a tighter seal formed by the valve structure.

In operation, a change in configuration of the housing cavity 36 of the valve housing 12 can displace and/or pressurize the fluid 62 in a manner to move the valve structure 40 to different open and closed positions, thereby selectively changing the diameter of the channel 50. Hence, by changing the configuration of the housing cavity 36 between a first configuration and a second configuration, the channel 50 is capable of receiving interventional devices of different diameters, such that the inner radial surface 46 forming the channel 50 can be positioned to form a seal along a longitudinal length of the interventional device. In addition, the diameter of the channel may be reduced to a degree such that the valve structure closes in on itself and forms a seal when no interventional device is present. The volume of the housing cavity in the first configuration can be reduced by, e.g., about 20%-30% when moved to the second configuration, while the volume of the valve chamber can remain substantially constant. For example, in the first configuration, the housing cavity can have a volume of about 0.9 cubic inches (14.8 ml), the volume of the valve chamber can be about 0.7 cubic inches (11.5 ml), the diameter of the channel can be about 0.4 inch (10 mm). In the second configuration, the housing cavity can have a volume of about 0.7 cubic inches (11.5 ml), the volume of the valve chamber can be about 0.7 cubic inches (11.5 ml), and the diameter of the channel can be about 0 mm. During movement to the second configuration, the fluid pressure within the valve chamber can be increased to about 10 psi (0.07 MPa).

The valve structure 40 can be made of any biocompatible material. In one example, the material of the valve structure 40 can have sufficient elasticity or compliance to have an expandable annular chamber, which can enhance sealing along the interventional device if required. When elastic, the valve structure may be biased in a fully open position, a fully closed position, or any position therebetween. In another example, the material of the valve structure can be non-compliant with minimal elasticity in order to have a substantially constant volume annular chamber. The valve structure 40 can be formed to have any desired channel diameter depending upon the size of the interventional device.

The valve structures used herein can be formed from elastomeric materials such as silicone, urethane, latex, or rubber, although any suitable composition known in the art for such purposes may be substituted. Alternative materials include polytetrafluoroethylene (PTFE); polyamide (e.g., nylon 12) material, a polyamide block copolymer (e.g., PEBA) and blends thereof (e.g., nylon 12/PEBA and PEBA/PEBA blends); polyolefins, polyolefin copolymers and blends thereof; polyesters (e.g., poly(ethylene terephthalate), PET); polyurethane copolymers with MDI, HMDI or TDI hard segment and aliphatic polyester, polyether or polycarbonate soft segment (e.g., PELLETHANE, ESTANE or BIONATE); and polyester copolymers with 4GT (PBT) hard segment and aliphatic polyester or polyether soft segments (e.g., HYTREL, PELPRENE or ARNITEL)). The rigidity of the valve structure may be considerably less than the rigidity of the components of the valve housing, resulting in a valve structure that is more flexible than the remaining structure. If desired, the valve structure, or preferably, the inner radial surface only of the valve structure, can be coated with a lubricious coating, such as parylene, to improve the lubricity of the surface and facilitate the passage of the interventional device therethrough.

The cannula body and the end cap can be made of a machined or injection molded relatively rigid polymeric material, such as such as acetal, polypropylene, ABS, nylon, PVC, polyethylene or polycarbonate. As illustrated, each of the aforementioned constituents includes a hollowed-out center portion to enable passage of an interventional device therethrough.

Operation of the valve assembly 10 to open and close the valve structure 40 will now be described. The valve structure 40 can be moved between the open and closed positions by relative axial movement between the end cap 16 and the cannula body 14 between a first position (FIG. 2) and a second position (FIG. 3) to vary the volume of the housing cavity. Although reference is made to first and second positions, the end cap may be movable through a number of positions intermediate the first and second positions, where the first position is a starting position and the second position is an ending position. In the first or starting position, the proximal end opening 30 is positioned a first distance away from the distal end opening 32 to form a housing cavity 36 with a larger volume. An end surface 65 of the end cap 16 that confronts an axial edge 67 of the cannula body 14 is shown to be positioned away from the edge 67. This first position can allow the valve structure 40 to be displaced radially outward away from the channel axis so that the diameter of the channel 50 can be increased to a larger diameter. The relative position of the end cap 16 and the cannula body 14 in the first or starting position may apply or increase a tension to valve structure 40 for radial movement away from the channel axis. Alternatively, to facilitate the movement of the valve structure to the open position, the valve structure may resiliently return to the open position when the valve structure is elastic and biased in an open position.

Figure 3:
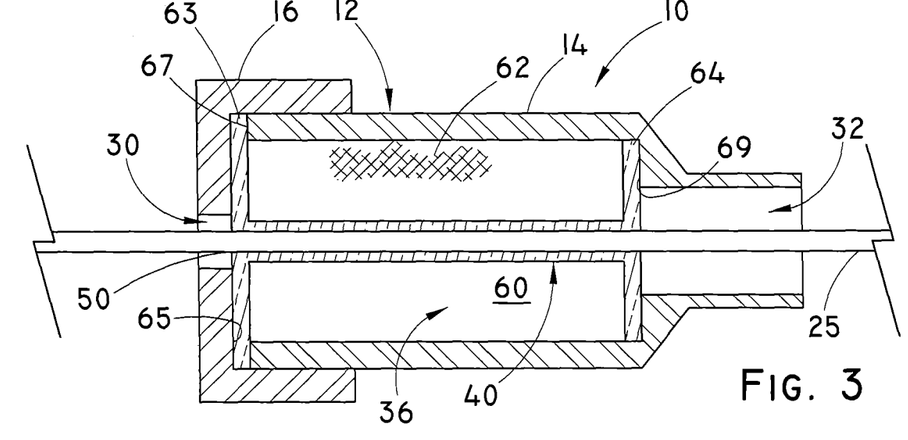
FIG. 3 is a cross-sectional view of the hemostatic valve device in FIG. 2, with a valve structure in a closed position.

In the second (intermediate or ending) position, the proximal end opening 30 is positioned a second, lesser distance away from the distal end opening 32 to form a housing cavity 36 with a smaller volume. The confronting surface 65 of the end cap 16 can be brought closer to the edge 67 of the cannula body 14, preferably substantially adjacent to or in contact with the edge 67 of cannula body 14. This second position can urge the fluid to be displaced in a manner that moves the valve structure 40 radially inward toward the channel axis so that the diameter of the channel 50 is reduced to a smaller diameter. The relative position of the end cap 16 and the cannula body 14 in the second position may reduce the tension of valve structure 40 for radial movement toward the channel axis. Alternatively, to facilitate the movement of the valve structure to the closed position, the valve structure may resiliently return to a closed position when the valve is elastic and biased in the closed position. As set forth above, the position of the confronting surface 65 of the end cap 16 relative to the axial edge 67 of the cannula body can be anywhere between the maximum and minimum positions, such as at an intermediate position, in order to vary the diameter of the channel 50 at a diameter between the first and second diameters.

In FIGS. 2 and 3, the proximal and/or distal end portions 63, 64 of the valve structure 40 may be attached within the valve housing 12 by any suitable attachment method such as an adhesive, welding, soldering, molded into the housing, or the like so that leakage of the fluid 62 within the valve chamber of the valve structure can be prevented. For example, the proximal end portion 63 can be attached to the interior surface 35 and/or to the confronting surface 65 of the end cap 16. The distal end portion 64 can be attached to a more distal portion of the interior surface 34 and/or a distal inner end 69 of the cannula body 14. In this manner, the fluid 62 can be sealed between the valve structure, the end cap, and the cannula body. In other examples, at least one of the proximal and distal end portions 63, 64 remain unattached to the respective housing wall as will be explained.

Figure 4:
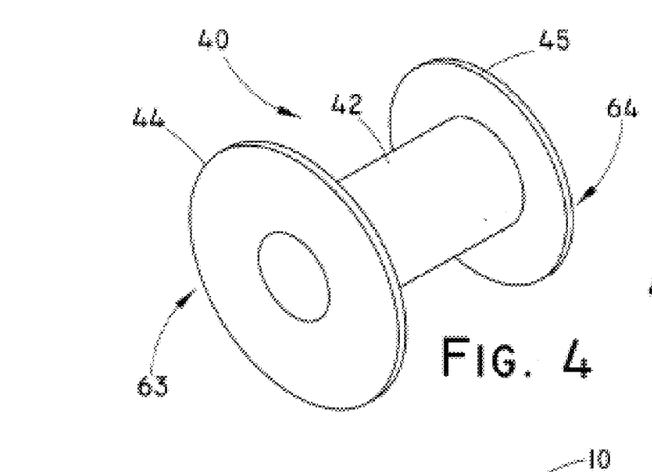
FIG. 4 is a perspective view of an example valve structure.

FIG. 4 depicts an example of the valve structure 40 shown in FIGS. 2-3. The valve structure 40 includes a generally cylindrical body 42 having an annular flange 44 at its proximal end portion 63 and an annular flange 45 at its distal end portion 64. Preferably one of the flanges, such as proximal flange 44, has a larger diameter than the other flange, as shown, e.g., in FIGS. 2-4. At least one of the annular flanges 44, 45 may have a rigidity sufficient to maintain its shape during the housing movement. The body 42 may have a rigidity less than the rigidity of the flanges 44, 45 so that the body 42 has a flexibility to be displaced during the housing movement. In addition to the valve structure 40 having the cylindrical cross-section as shown, the valve structure can have other cross-sectional configurations. Non-limiting examples of such configurations include a valve body having an accordion-type shape or an hourglass shape, as well as the valve body having other cross-sectional geometric shapes such as rectangular, triangular, diamond, or elliptical, which are described in U.S. Pat. No. 7,172,580, which is incorporated herein by reference in its entirety.

In other examples, the proximal and/or distal end portions 63, 64 of the valve structure 40 may be positioned in the valve housing 12 in the absence of a permanent attachment method, i.e., in the absence of adhesive, welding, soldering, etc. To this end, the proximal and/or distal end portions 63, 64 of the valve structure 40 may be coupled to the valve housing 12 with a mechanical interference fit in a manner to form a suitable mechanical seal and permit relative rotational movement between the end cap 14 and the cannula body 16. This arrangement can inhibit substantial twisting of valve structure 40, and preferably without any twisting, thereby permitting a substantial portion of the inner radial surface of the valve structure to sealably engage one another or the interventional device when received in the channel.

Figure 5:
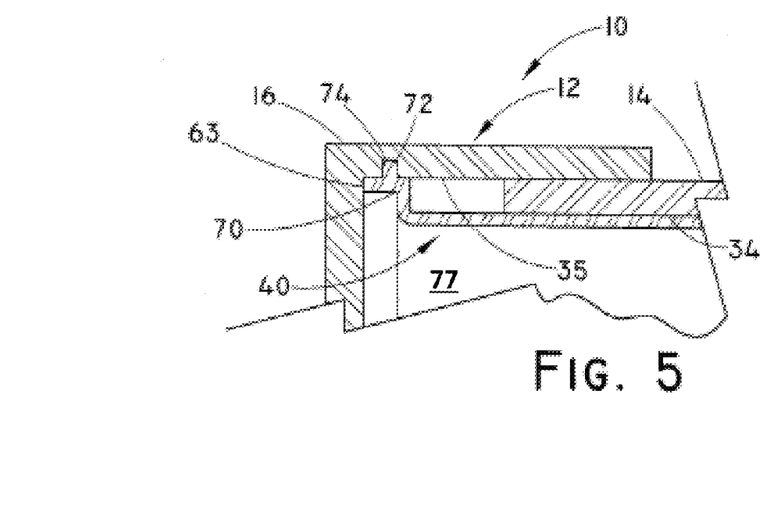
FIG. 5 is a partial cross-sectional view of a hemostatic valve device, depicting one example of a mechanical seal formed between a valve structure and a valve housing.
Figure 6:
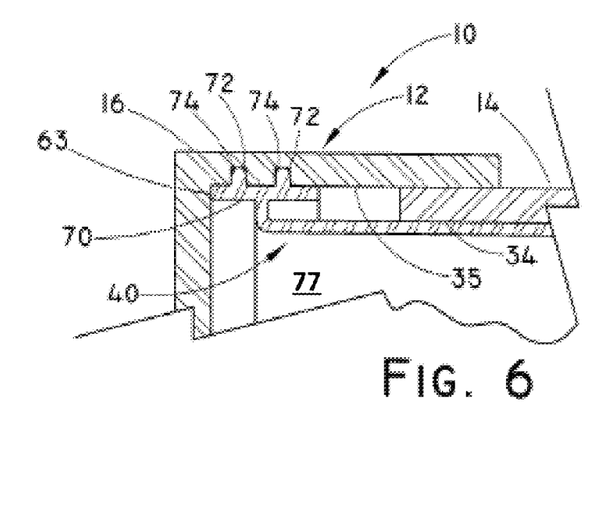
FIG. 6 is a partial cross-sectional view of a hemostatic valve device, depicting another example of a mechanical seal formed between a valve structure and a valve housing.
Figure 7:
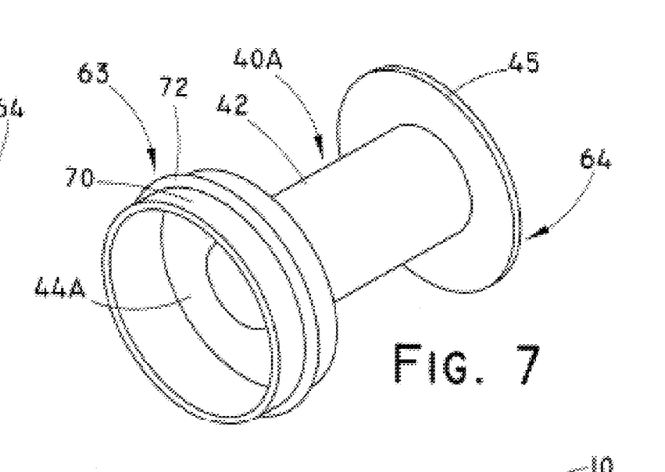
FIG. 7 is a perspective view of another example valve structure.

FIGS. 5-6 depict embodiments with a mechanical seal. The valve structure 40 can include one or more ring structures 70 at least at one of the proximal and distal end portions 63, 64. For example, FIG. 7 depicts another example of a valve structure 40A, similar to the valve structure 40, including the ring structure 70 at the proximal end portion 63. The ring structure 70 can be configured to maintain engagement against the interior surface 35 of the end cap 16 and/or against the interior surface 34 of the cannula body 14 during movement of the valve structure. The annular flange 44A can couple the ring structure 70 to the body 42. The ring structure may be formed of the rigid material of the annular flange to facilitate the ring structure maintaining its shape and contact with the housing during movement of the housing.

The ring structure 70 can be relatively more rigid than the more flexible body 42 radially depending from the ring structure. The longitudinal length of the ring structure 70 may be sized to increase the overall sealing surface area contact between the ring structure and the housing wall for enhancing sealability. A sealing member can be applied between the outer walls of the valve structure and the inner walls of the housing. For example, one or more outer radial protrusions 72 can be formed circumferentially along an outside portion of the valve structure 40. Optionally, a separate O-ring can be coupled to the valve structure 40 in place of the radial protrusion; however further description below will focus on valve structures with the radial protrusion. The radial protrusion 72 may be used in combination with the ring structure as shown in FIG. 7. The radial protrusion 72 can be inserted within a corresponding inner groove 74 formed in the interior surface 35 of end cap 16 and/or against interior surface 34 of housing body 14. The radial protrusion and the inner groove can be sized such that, in addition to forming a suitable mechanical seal to prevent leakage, the end cap can be rotated relative to the cannula body without substantial twisting of the valve structure.

In FIG. 5, a single radial protrusion 72 formed along the ring structure 70 of the valve structure 40 is inserted within a single inner groove 74 of the interior surface 35 of the end cap 16 to form a mechanical seal. Here, the mechanical seal is formed external to the annular chamber 77 of the valve structure 40. The longitudinal length of the ring structure 70 may extend beyond the edges that define the inner groove 74. In one example, the ring structure 70 may have a portion that extends farther within the annular chamber 77, so that the fluid 62 may exert a pressure along this portion to enhance sealability.

In FIG. 6, a pair of radial protrusions 72 formed along the ring structure 70 of the valve structure 40 is inserted within a pair of corresponding inner grooves 74 of the interior surface 35 of the end cap 16 to form a mechanical seal. One corresponding radial protrusion and inner groove set can be longitudinally disposed relative to the annular chamber to define a mechanical seal external to the annular chamber 77. Another corresponding radial protrusion and inner groove set can be longitudinally disposed relative to the annular chamber to define a mechanical seal internally with respect to the annular chamber 77. It is contemplated that various configurations and number of radial protrusions and inner grooves, external, internal, or both, may be used. The radial protrusion and inner groove configuration formed internally within the annular chamber 77 of the valve structure 40 may be particularly beneficial for sealability between the valve structure and the valve housing. For instance, fluid within the annular chamber 77, when displaced and/or pressurized as described herein, can increase the contact pressure between the ring structure 70 and the interior surface 35, as well as the radial protrusion 72 and the inner groove 74 of the valve structure 40. To this end, it is further contemplated that the single radial protrusion and groove combination, shown in FIG. 5 that forms the mechanical seal external to the annular chamber, may be arranged to form a mechanical seal internally within the annular chamber, similar to the internal arrangement in FIG. 6. It is further contemplated that the inner wall of the housing may include the radial protrusion and the valve structure may include the groove.

Figure 8:
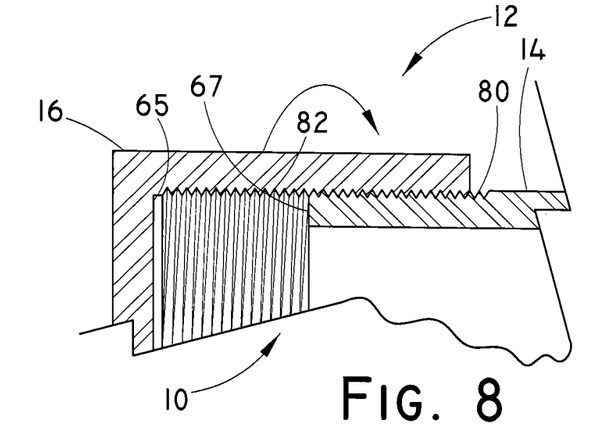
FIG. 8 is a partial cross-sectional view of a hemostatic valve device, depicting a rotatable cap relative to a main valve housing.

Relative axial movement between the end cap 16 and the cannula body 14 may be further enhanced by a controller mechanism that allows for incremental changes in the diameter of the channel 50. FIG. 8 depicts one example of the controller mechanism having a threaded attachment between the cannula body 14 and the end cap 16. A threaded portion 80 may be formed in the cannula body 14, which corresponds with a threaded portion 82 formed in the end cap 16. Thus, for example, relative rotation between the end cap 16 and the cannula body 14 can move the end cap 16 between the first position (FIG. 2) and the second position (FIG. 3). Preferably, the threaded attachment can provide the clinician with the capability of adjusting the diameter of the channel 50 and thus the seal formed by the valve structure 40. It is contemplated that the threaded portions can be further configured, e.g., by varying the thread pitch, to correlate the number of rotations of the end cap 16 to a degree of diameter change of the channel 50. For example, one rotation of the end cap 16 relative to the cannula body 14, resulting in, about 1 mm of relative axial translation of the cap, can equal about 1 mm change in diameter of the channel 50.

A locking mechanism may be included between the cannula body 14 and the end cap 16. The locking mechanism can secure the relative position between the end cap 16 and the cannula body 14 in a fixed position once the desired diameter of the channel has been achieved. For example, a clamp may be applied to the end cap 16 and the housing body 14 to fix the relative position therebetween.

Figure 9A:
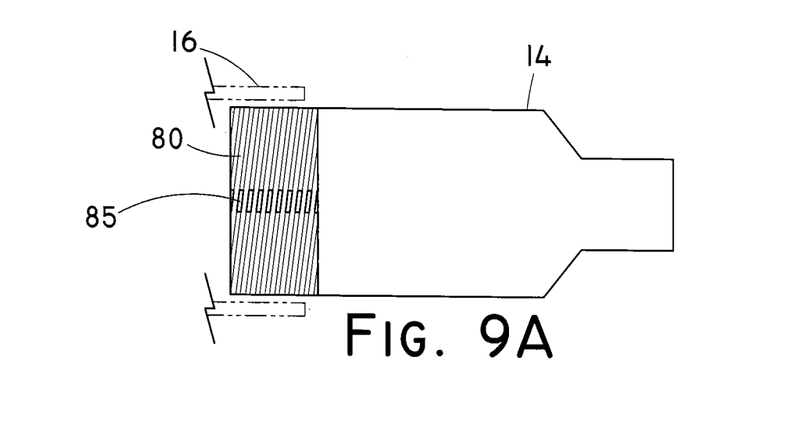
FIG. 9A is a side view of a main valve housing illustrating a portion of a locking mechanism.
Figure 9B:
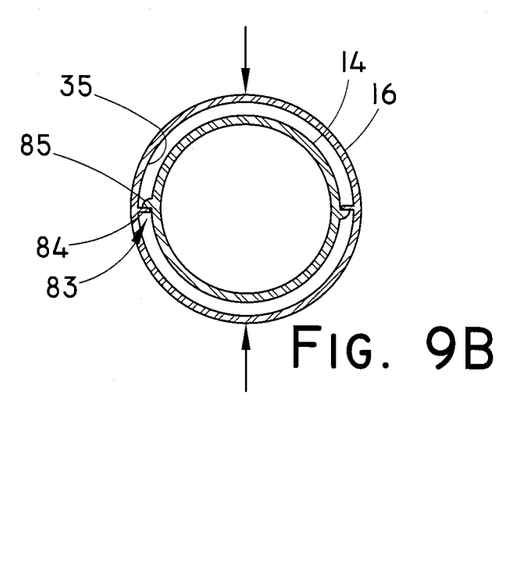
FIG. 9B is a transverse sectional view of an end cap and a main valve housing with a pawl and a detent of the locking mechanism.

In another example, a locking mechanism 83 can include a ratchet mechanism having ratchet features, such as a combination of a pawl 84 and a detent 85, as shown in FIG. 9B. For example, FIG. 9A shows the cannula body 14 having a series of detents 85 formed within the threaded portion 80. The detent may rise above the surface having the threaded portion 80 formed therein or be contained within the threaded portion. FIG. 9B shows a pair of pawls 84 formed in the interior surface 35 of the end cap 16 engaging with a corresponding pair of detents 85. The detent 85 may be shaped to have a planar surface generally orthogonal to the outer surface of the cannula body to prevent the pawl 84 from travelling in one direction, and an inclined surface to allow the pawl 84 to travel in the opposite direction. It can be appreciated by those skilled in the art that any number of detents besides one per every 180 degrees can be arranged along the threaded portion for greater or lesser incremental movement, such as, e.g., one per 90 degrees, 60 degrees, or 30 degrees.

The ratchet mechanism can allow for incremental relative movement between the end cap and the cannula body in one direction, e.g., in closing the valve structure, and inhibit movement in the opposite direction, e.g., in opening the valve structure. To this end, the end cap 16 may be freely rotated in one direction relative to the cannula body 14 in a manner to reduce the diameter of the channel 50. However, when a suitable seal is formed with the valve structure, the pawl 84 can be selectively engaged with the detent 85 to inhibit rotation of the end cap 16 in the opposite direction. To readjust for the diameter of the channel 50, the pawl 84 can be selectively disengaged from the detent 85 to permit rotation of the end cap in the opposite direction. FIG. 9B shows the body of the end cap 16 may be conformable in a manner so that diametric squeezing of the end cap 16 along portions, shown by the arrows, circumferentially offset, such as 90 degrees, from the pawls 84 can urge the pawls to be displaced radially outward for disengagement from the detent 85. After disengagement, the end cap can slide or be rotated relative to the cannula body to a desired position.

The number of ratcheting members such as the pawl and detent on each of members 14 and 16 is exemplary only, and other numbers of such ratcheting members may be substituted, as long as the objective of inhibiting recoil of rotatable end cap 16 may be met. In addition, the ratcheting members may be rib-like such as described in the previously incorporated-by-reference U.S. Pat. No. 7,172,580, or a combination of ribs and grooves may also be utilized to inhibit recoil. For example, rib members can be provided on the cannula body and corresponding grooves or ribs can be provided on the end cap 16. This arrangement can be reversed if desired. That is, rib members may be provided on the end cap and the corresponding grooves or ribs may be provided on the cannula body. The ratcheting members can be positioned in complementary arrangements other than those specifically described to enable the valve structure to provide a seal around devices of varying diameters. If desired, the spacing of the ratcheting members can be optimized depending upon the diameter of the device passing through. The ratcheting members need not be evenly spaced, and they can be offset or otherwise varied depending upon the configuration and type of device passed therethrough, as long as the ratcheting feature may be obtained. Other ratcheting mechanisms may be substituted for achieving this action.

Figure 10:
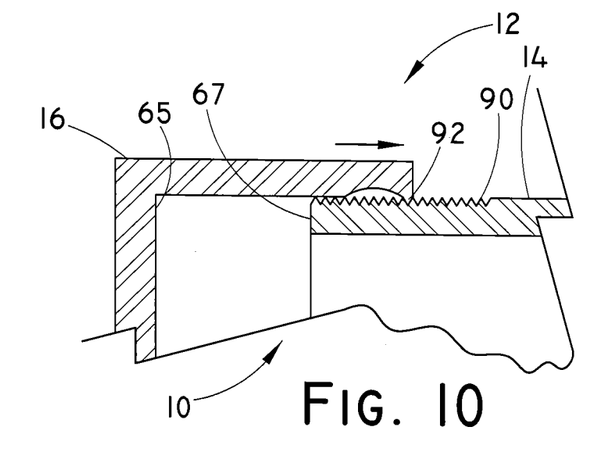
FIG. 10 is a partial cross-sectional view of a hemostatic valve device, depicting a slidable cap relative to a main valve housing.

FIG. 10 depicts another example of the controller mechanism having a sliding pawl and groove configuration between the cannula body 14 and the end cap 16. A series of ratchet grooves 90 can be circumferentially formed in the cannula body 14. The grooves 90 are sized to receive a tip of a pawl device 92 that extends from the end cap 16. Thus, relative sliding between the end cap 16 and the cannula body 14 can move the end cap 16 between the first position (FIG. 2) and the second position (FIG. 3). The ratchet grooves and pawl configuration can provide the clinician with the capability of adjusting the diameter of the channel 50 and thus the seal formed by the valve structure. It is contemplated that the grooves and the sliding pawl configuration can be further configured to correlate the number of grooves to a degree of diameter change of the channel 50. For example, the translation of the end cap 16 relative to the cannula body by one groove can equal about 1 mm change in diameter of the channel 50. A locking mechanism, such as described above, may be also included. In one example, after a suitable seal is formed, the tip of the pawl 92 can be configured to selectively reside in one of the ratchet grooves 90 to inhibit slidability of the end cap 16 in one direction. The pawl 92 can be selectively disengaged from the groove 90, such as by diametrically squeezing the end cap as shown in FIG. 9B, to permit sliding of the end cap 16 in the opposite direction.

A sealable relationship between the end cap 16 and the cannula body 14 may be beneficial to further inhibit leakage of the fluid from the valve structure 40. For example, engaging surfaces between the end cap 16 and the cannula body 14 may be configured to provide enhanced sealability. An internal sealing structure such as an O-ring, a sealing tape, and/or a sealant may be applied between the engaging surfaces. In one example, a sealing tape such as Teflon tape can be applied between the threaded portions of the end cap and the cannula body. Optionally, an external sealing structure may be externally applied between the end cap 16 and the cannula body 14 to further enhance sealability.

Figure 11:
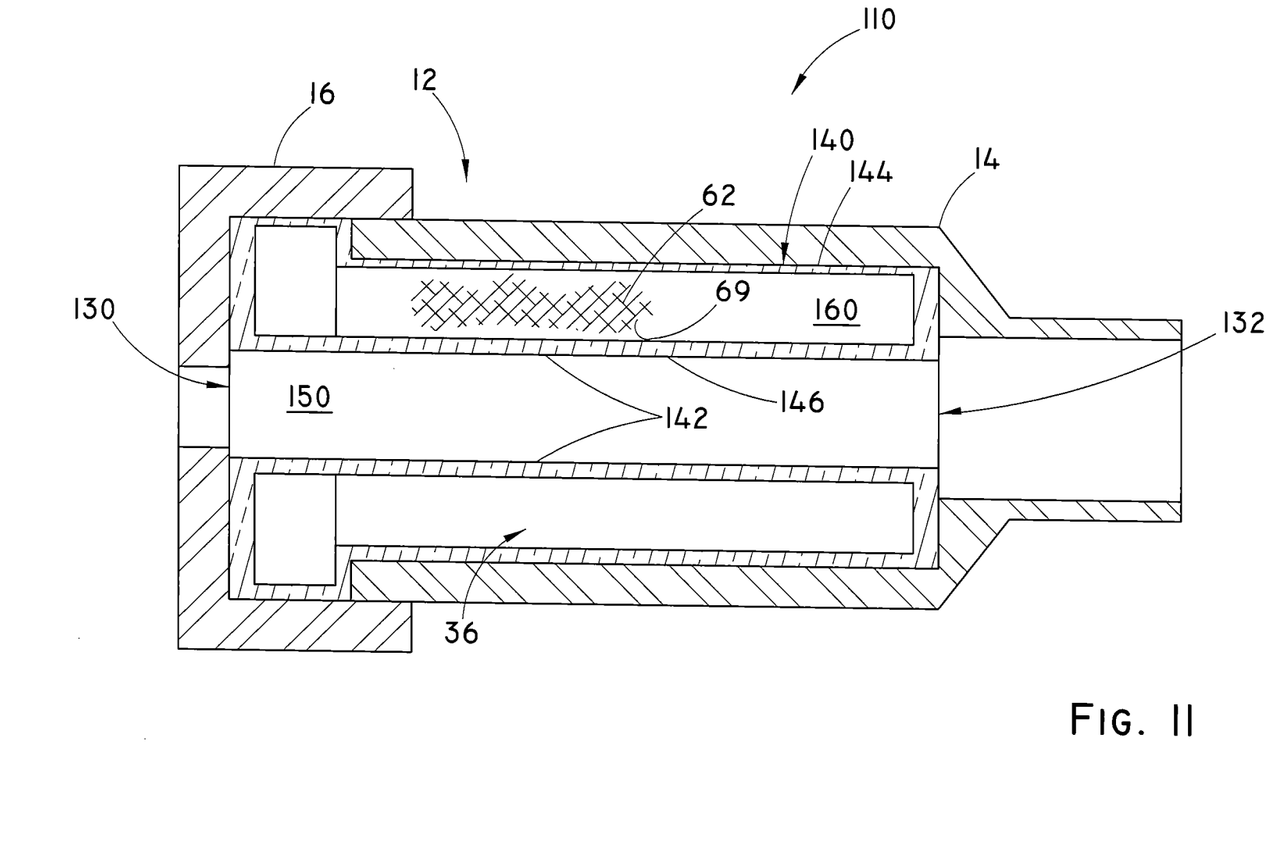
FIG. 11 is a cross-sectional view of another example of a hemostatic valve device.

FIG. 11 shows another embodiment of a hemostatic valve assembly, referenced as numeral 110, having at least some of the features described above with respect to the valve assembly 10. Here, the valve assembly 110 includes a toroidal valve structure 140 disposed within the housing cavity 36. The valve structure 140 can have an interior wall 142 and an exterior wall 144 to define an annular valve chamber 160 of the toroidal structure. The valve structure may have annular flanges as described above at its proximal and/or distal ends that are made of a more rigid material than the more flexible interior and exterior walls. An inner radial segment 146 of the interior wall 142 can define a longitudinal channel 150 within the housing cavity 36 between the proximal and distal end openings 130, 132. The valve structure 140 may be attached to the valve housing 12 or can remain unattached to the housing. The fluid 62 can fill the valve chamber 160, which is contained entirely within the toroidal valve structure. Movement of the valve structure 140 between the open and closed positions is as a result of the relative position between the end cap 16 and the cannula body 14 between the first position (FIG. 2) and the second position (FIG. 3), as described with reference to the previous embodiments. Since the walls of valve structure 140 contain the fluid, a sealable relationship between the end cap, the cannula body, and/or the valve structure may not be necessary. The controller mechanism and/or the locking mechanism, as described above, may be further included with the valve assembly 110 to control the relative movement between the end cap and the cannula body.

Figure 12:
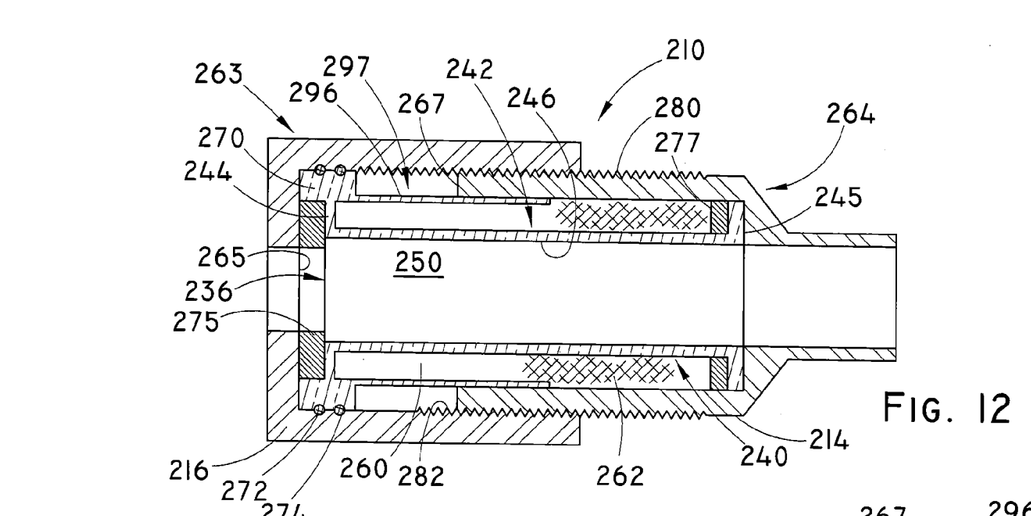
FIG. 12 is a cross-sectional view of another example of a hemostatic valve device, with a valve structure in an open position.
Figure 13:
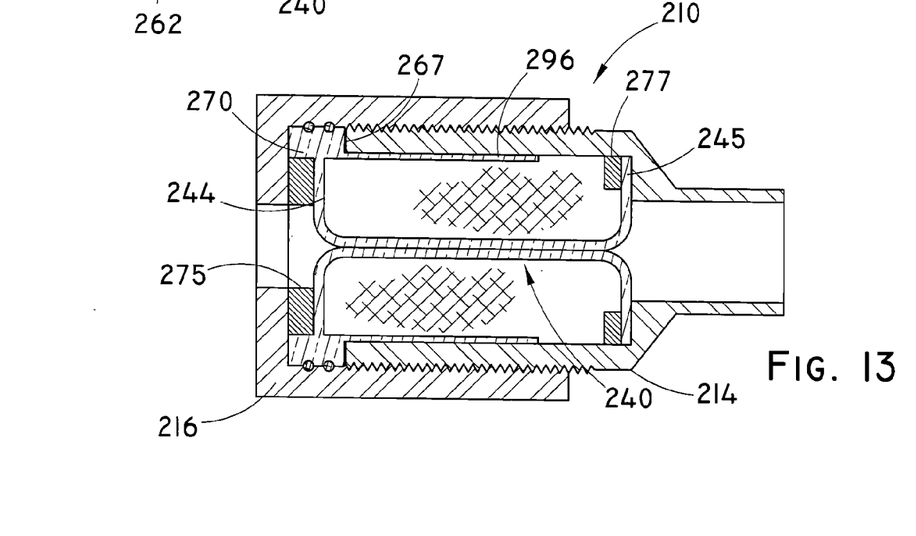
FIG. 13 is a cross-sectional view of the hemostatic valve device in FIG. 12, with the valve structure in a closed position.

FIGS. 12-13 illustrate another example of a hemostatic valve device, referenced as numeral 210, having at least some of the features described above with respect to the valve assemblies 10, 110. Here, the valve assembly 210 includes the valve structure 240, generally similar to the valve structure 40A shown in FIG. 7, disposed within the housing cavity 236. The valve structure 240 can include a ring structure 270 at a proximal end 263 and an annular flange 245 at a distal end 264, with cylindrical body 242 therebetween. The ring structure 270 may be coupled to the body 242 with annular flange 244. The valve structure 210 is arranged within the housing cavity 236 to define annular valve chamber 260. The inner radial surface 246 can define the channel 250 within the housing cavity 236. The ring structure 270 may be structured to fit snugly against the interior surface of the end cap 216. One or more sealing members, such as O-rings 272, can be disposed around the ring structure and inserted within one or more inner grooves 274. A first support member 275, such as a ring, can be placed between the annular flange 244 and the end surface 265 of the end cap 216 to prevent movement of the ring member 270 away from the end cap and the annular flange in the longitudinal direction. A second support member 277, such as a ring, can be placed against the inner surface of the annular flange 245 to retain the annular flange 245 in a secured position. The first and second support members may be formed integrally with the housing or as separate components disposed as shown in the figures. Preferably, the proximal end 263 of the valve structure 240 is a free end, that is, is not securely fixed to the end cap 216, thereby allowing the end cap to be rotated relative to the proximal end of the valve structure without substantial twisting of the valve structure. The distal end of the valve structure may be fixed securely to the housing.

The end cap 216 can have the threaded portion 282 that is in threaded contact with the threaded portion 280 of the cannula body 214. A sealing tape (not shown) can be interposed between the threaded portions 280, 282 to inhibit substantial leakage from this region of the valve device. The fluid 262 can fill the valve chamber 260. A sealing apron 296 may extend axially from the ring structure 270 toward the cannula body. The sealing apron 296 can be in the form of a ring, which may be rigid to maintain its shape. A pocket 297 can be formed between the sealing apron 296 and the end cap 216 for receiving the end 267 of the cannula body. According to FIG. 12, the sealing apron 296 can extend past the end 267 of the cannula body and along the inner wall of the cannula body. The sealing apron can be sized to maintain intimate contact along the inner surface of the cannula body during relative movement of the end cap. Relative axial movement between the end cap 216 and the cannula body 214 is as a result of the rotation of the end cap 216 relative to the cannula body 214 between the first position (FIG. 12) and the second position (FIG. 13). As a result, the valve structure 240 can move between the open and closed positions, and the channel 250 can be moved between the first diameter and the second diameter, respectively. FIG. 13 depicts the valve structure 240 sealing entirely against itself to effectively close the channel 250. The end 267 of the cannula body 214 can engage the confronting end of the ring structure 270 to enhance sealability. The controller mechanism and/or the locking mechanism, as described above, may be further included with the valve assembly 210 to control the relative movement between the end cap and the cannula body.

Figure 14:
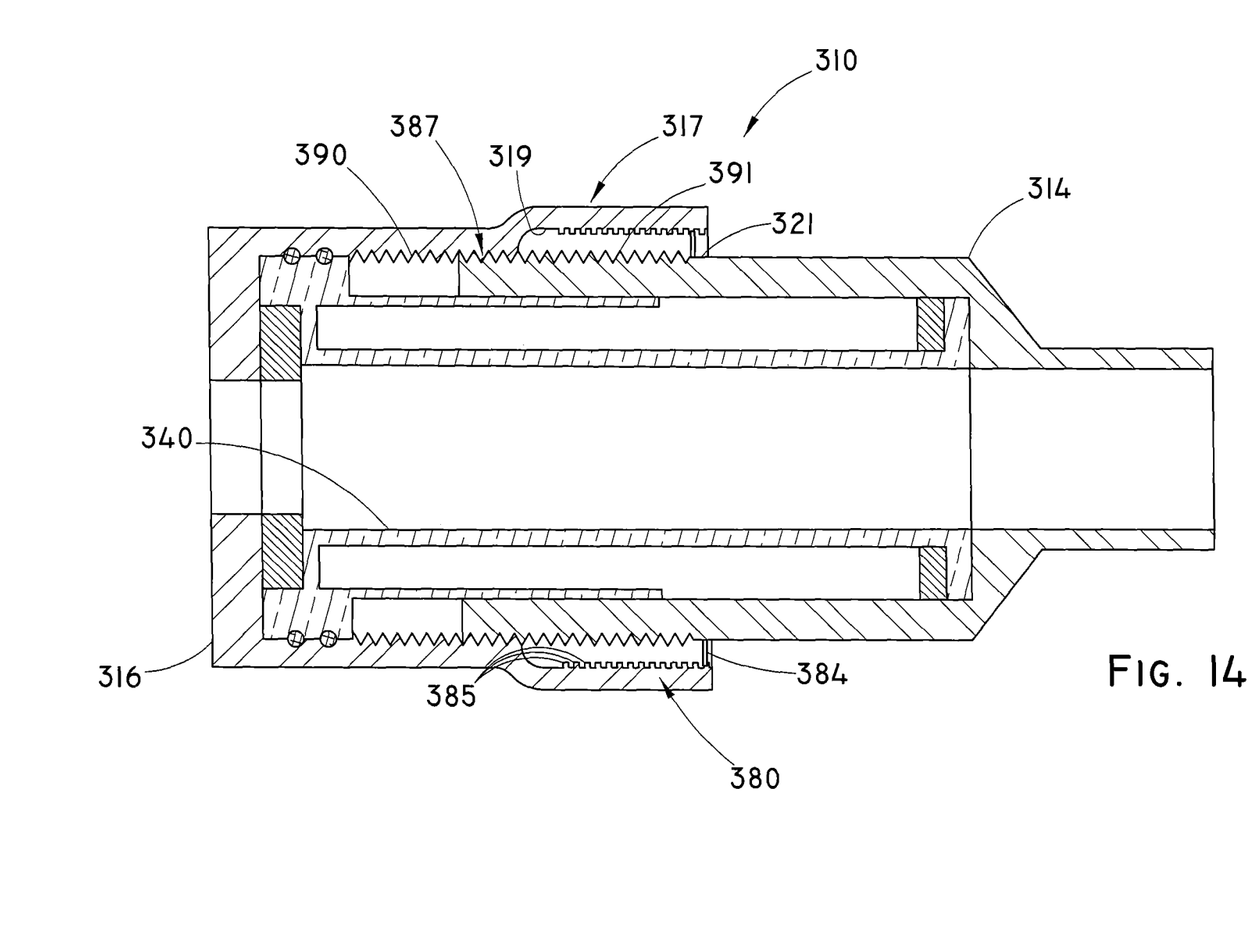
FIG. 14 is a cross-sectional view of another example of a hemostatic valve device.

FIG. 14 illustrates another example of a hemostatic valve device, referenced as numeral 310, having at least some of the features described above with respect to the valve assemblies 10, 110, and 210, having a ratchet system and threadable engagement. In this example, the end cap 316 has an end portion 317 that is spaced away from the outer circumference of the cannula body 314. An inner surface 319 along the end portion 317 and the outer surface 321 of the cannula body 314 may include one or more of the ratchet features shown in FIGS. 9A-9B. For example, the inner surface 319 of the end cap 316 can have the series of detents 385 formed within a threaded portion 380, while the outer surface 321 of the cannula body 314 can have the pawls 384 fixed on the outer surface. The end portion 317 may be made of a conformable material that is attached to the end cap 316. Optionally, the end portion 317 may be integrally formed with the end cap 316. In this instance, the end portion 317 may have a thinner wall relative to the wall thickness of the body of the end cap to facilitate conforming the end portion to release the detents from the pawls. The portion 387 of the end cap adjacent the end portion 317 can be sealably engaged with the cannula body, for example, such as shown in FIG. 12. The adjacent portion 387 of the end cap 316 is shown with a threaded portion 390 engaged with another threaded portion 391 of the cannula body 314. The threaded portions 390, 391, 380 can have substantially the same configuration (i.e., thread angle, pitch, threadform) such that relative rotation between the end cap and the cannula body will permit the pawls 384 to follow the threaded portion 380 to engage the detents 385. The ratchet system permits incremental control of the change in diameter of the channel formed by the exemplary valve member 340 shown in FIG. 14.

Drawings in the figures illustrating various embodiments are not necessarily to scale. Some drawings may have certain details magnified for emphasis, and any different numbers or proportions of parts should not be read as limiting, unless so-designated in the present disclosure. Although certain features of the valve device are only described with respect to certain embodiments and figures, it can be appreciated by those skilled in the art that the invention is not limited to any one of these features or embodiments but may reside in two or more combined features or embodiments together. Thus, those of skill in the art will appreciate that embodiments not expressly illustrated herein may be practiced within the scope of the present invention, including those features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention

What is claimed is:

1. A hemostatic valve device comprising: a housing having a first end opening, a second end opening, and an interior surface defining a housing cavity between the first and second end openings; a valve structure disposed within the housing cavity and coupled to the housing to define an annular chamber within the housing cavity, the valve structure having an inner radial surface defining a longitudinal tubular channel within the housing cavity at least partially between the first and second end openings; wherein the housing is movable between a first configuration whereby the housing cavity has a first volume and the channel has a first diameter, and a second configuration whereby the first and second end openings are closer to one another, the housing cavity has a second volume that is less than the first volume, and the channel has a second diameter that is less than the first diameter; wherein the annular chamber has a substantially constant volume in the first configuration when the housing cavity has a first volume and in the second configuration when the housing cavity has a second volume that is less than the first volume.

2. The device of claim 1, wherein the annular chamber has a constant volume.

3. The device of claim 1, wherein the annular chamber includes a substantially incompressible fluid.

4. The device of claim 1, wherein the valve structure further comprises a toroidal valve structure.

5. The device of claim 1, wherein the valve structure further comprises a ring segment formed along an axial end of the valve structure, the ring segment being configured to remain in engagement with the interior surface of the housing during movement of the housing.

6. The device of claim 5, wherein the valve structure further comprises a sealing member, the interior surface of the housing including an inner groove formed therein to receive the sealing member, the sealing member disposed along a portion of the ring segment and received within the inner groove.

7. The device of claim 1, wherein the housing further comprises a first portion and a second portion, and wherein relative axial movement between the first and second portions causes movement of the housing between the first and second configurations.

8. The device of claim 7, wherein the first and second portions are threadably engaged with one another so that relative rotation between the first and second portions causes movement of the housing between the first and second configurations.

9. The device of claim 7, wherein the first and second portions of the housing are engaged in a ratchet manner with one another so that relative axial sliding between the first and second portions causes movement of the housing between the first and second configurations.

10. The device of claim 7, wherein the valve structure comprises a first end coupled to the first portion and a second end coupled to the second portion, wherein one of the first and second ends of the valve structure is securely fixed to the respective first or second portions, and the other of the first or second ends is coupled to the respective first or second portions to prevent substantial twisting of the valve structure in response to relative axial movement between the first portion and the second portion.

11. A hemostatic valve device comprising: a housing having a first end opening, a second end opening, and an interior surface defining a housing cavity disposed between the first and second end openings, the housing including an end cap and a cannula body; a bladder structure disposed within the housing cavity and coupled between the end cap and the cannula body of the housing to define a substantially constant volume annular chamber within the housing cavity, the bladder structure having an inner radial tubular surface defining a channel within the housing cavity at least partially between the first and second end openings; and a fluid disposed within the annular chamber of the bladder structure; where relative axial movement between the end cap and the cannula body varies a volume of the housing cavity and displaces the bladder structure between an open configuration and a sealed configuration to move the channel between a first diameter and a second diameter, respectively;

wherein the end cap is movable relative to the housing body between a first position, whereby the fluid exerts a first pressure on the valve structure in the open configuration, and a second position, whereby the fluid exerts a second pressure on the valve structure in the sealed configuration that is greater than the first pressure.

12. The device of claim 11, wherein the bladder structure further comprises a ring portion along one end of the bladder structure, and a sealing apron extending axially from the ring portion to engage an inner surface of the cannula body.

13. The device of claim 12, wherein the interior surface of the housing includes an inner groove, and an end portion of the bladder structure comprises a radial protruding ring that is received within the inner groove to form the mechanical seal between the bladder structure and the housing.

14. The device of claim 13, wherein the inner groove is disposed longitudinally relative to the annular chamber of the bladder structure so that an increase in fluid pressure within the bladder structure increases the radial pressure of the radial protruding ring within the inner groove.

15. The device of claim 11, wherein the end cap has an end portion that is spaced from a corresponding outer surface of the cannula body, where the end portion and the corresponding outer surface comprises a ratcheting mechanism to selectively inhibit relative movement between the end cap and the cannula body.

\* \* \* \* \*